United States Patent [19]
Askanazi et al.

[11] Patent Number: 5,140,045
[45] Date of Patent: * Aug. 18, 1992

[54] METHOD FOR IMPROVING VENTILATION DURING SLEEP AND TREATING SLEEP RELATED VENTILATION ABNORMALITIES OF NEONATES

[75] Inventors: Jeffrey Askanazi, Haworth, N.J.; Susan Trimbo, Evanson, Ill.

[73] Assignee: Clintec Nutrition Co., Deerfield, Ill.

[*] Notice: The portion of the term of this patent subsequent to May 21, 2008 has been disclaimed.

[21] Appl. No.: 656,563

[22] Filed: Feb. 15, 1991

Related U.S. Application Data

[63] Continuation-in-part of Ser. No. 443,765, Nov. 30, 1989, Pat. No. 5,017,616.

[51] Int. Cl.⁵ ............................................. A61K 31/195
[52] U.S. Cl. ..................................................... 514/561
[58] Field of Search ................................ 514/561, 923

[56] References Cited

U.S. PATENT DOCUMENTS

| | | | |
|---|---|---|---|
| 4,209,531 | 6/1980 | Berry | 514/561 |
| 5,017,616 | 5/1991 | Askanazi | 514/561 |

FOREIGN PATENT DOCUMENTS 2037161 7/1980 United Kingdom .

OTHER PUBLICATIONS

Ghadimi et al., Total Parenteral Nutrition for Preventing and Treatment of RDS, p. 573 (1973).
J. Takala et al., Changes in Respiratory Control Induced by Amino Acid Infusions, Critical Care Medicine, vol. 16, No. 5, (May 1988) pp. 465–469.
The Merck Manual, 14th edition (1982) p. 1763.

Primary Examiner—Frederick E. Waddell
Assistant Examiner—Raymond J. Henley, III
Attorney, Agent, or Firm—Hill, Van Santen, Steadman & Simpson

[57] ABSTRACT

A method for improving ventilation during sleep and treating sleep-related ventilation abnormalities in an infant. To this end, the present invention provides a method of using branched-chain amino acids as an effective therapy for apnea of prematurity. The branched-chain amino acid composition can be administered either parenterally or enterally, and can be administered alone or in combination with other nutrients.

19 Claims, 2 Drawing Sheets

METHOD FOR IMPROVING VENTILATION DURING SLEEP AND TREATING SLEEP RELATED VENTILATION ABNORMALITIES OF NEONATES

BACKGROUND OF THE INVENTION

This is a continuation-in-part of U.S. patent application Ser. No. 443,765, filed Nov. 30, 1989, now U.S. Pat. No. 5,017,616.

The present invention relates to a method for the use of branched-chain amino acids to improve ventilation during sleep. More specifically, the present invention relates to a method for treating sleep related ventilation problems, such as apnea.

Sleep apnea is recognized as a serious and often life threatening abnormality of the breathing pattern. See, Kales, et al, *Sleep Disorders: Sleep Apneas and Narcolepsy*, Ann. Intern. Med., 106:434-443, 1987. The morbidity of sleep apnea is due to a decrease oxygenation of the arterial blood and carbon dioxide retention secondarily to alveolar hypoventilation.

The condition of sleep apnea has been defined as the cessation of breathing for at least 10 seconds, that occurs at least 30 times during a 7 hour period of sleep. This definition, however, is based on sleep laboratory studies and accordingly, is not clinically applicable. Instead, arterial oxygen desaturation during sleep is the critical factor in determining sleep apnea. See, Block, et al, *Sleep Apnea, Hypopnea and Oxygen Desaturation in Normal Subjects*, New England Journal of Medicine, 300:513-517, 1979.

The sleep apnea syndrome has been observed as a primary disease in otherwise healthy subjects. Apneas can be divided into three sub-groups: central; obstructive; and mixed. Abnormal respiratory control is believed to be involved in all types of sleep apneas. Apneic breathing patterns during sleep occur also in association with certain other conditions, such as: morbid obesity; coronary disease; and congestive heart failure. See, Walse, et al, *Upper Airway Obstruction in Obese Patients With Sleep Disturbances and Somnolence*, Ann. Intern. Med. 76: 185-192, 1972; DeOlazabal, et al, *Disordered Breathing and Hypoxia During Sleep in Coronary Artery Disease*, Chest, 82:548-552, 1982; and Dark, et al, *Breathing Pattern Abnormalities and Arterial Desaturation During Sleep in the Congestive Heart Failure Syndrome, Improvement Following Medical Therapy*, Chest, 91:833-836, 1987. Patients recovering from anesthesia also frequently exhibit apneic breathing patterns.

Most patients with sleep apnea snore heavily and many exhibit severe oxygen desaturation. Oxygen desaturation during sleep may be associated with pulmonary and systematic hypertension and cardiac arrhythmias. Tilkian, et al, Sleep-Induced Apnea Syndrome, *Prevelance of Cardiac Arrhythmias and Their Reversal After Tracheostomy*, Am. J. Med. 63(3):348-358, 1976; and Tilkian, et al, *Hemodynamics in Sleep-Induced Apnea*, Am. Intern. Med. 85(6):714-719, 1977.

The typical management of sleep apnea syndrome is to relieve upper air obstruction and to also stimulate respiratory activity. Typically, pharmacologic techniques are utilized to achieve these goals. However, drug therapy alone is not usually effective in relieving sleep apneas. Moreover, such drug therapies are often associated with adverse side effects.

One drug that is used is Medroxyuprogesterone acetate (MPA). MPA has been found to be a moderate, sustained ventilatory stimulant in man. MPA reduces sleep apnea in less than half of all patients. Strohl, et al, *Progesterone Administration and Progressive Sleep Apneas*, J.A.M.A., 245:1230-1232, 1981. But, MPA causes impotence in men and therefore the desirability and use of this drug is limited.

Another drug, protiptyline has been found to improve sleep apnea in some patients. This drug, however, is associated with such serious side effects such as: constipation; urinary retention; ataxia; and confusion. Brownell, et al, *Protiptyline in Obstructive Sleep Apnea*, New England Journal of Medicine, 307:1037-1042, 1982.

Accordingly, although pharmacologic interventions can be, in some cases, effective in decreasing the frequency and duration of sleep apneas, and the extent of oxygen desaturation in patients, the usefulness of such drug therapy is limited due to the adverse side effects of such drugs. Therefore, there is a need for an improved therapy for treating patients with sleep apnea.

Apnea of prematurity is one of the most common disorders that afflict premature infants. A number of theories have been proposed regarding its pathogenesis. Likewise, a variety of methods of treatment, having a range of effectiveness, have been proposed. However, apnea of prematurity remains a perplexing problem that is potentially life threatening.

In premature infants, periodic breathing, respiratory pauses of more than 3 seconds in duration with normal respiratory intervals of 20 seconds or less is considered a normal respiratory pattern. Kelly et al, *Periodic Breathing in Infants with Near-Miss Sudden Infant Death Syndrome*, Pediatrics, 63:964 (1982). In contrast, apnea of prematurity is defined as either: 1) cessation of breathing for a period of 20 seconds or more; or 2) a period of time without respiration that is accompanied by cyanosis, bradycardia, hypotonia, metabolic acidosis, or pallor. See, Martin et al, *Respiratory Problems*, Care of the High Risk Neonate, 3rd Edition (1986), pp. 171-201; and Klesh et al, *Apnea of Prematurity Current Theories of Pathogenesis and Treatment*, Neonatal Intensive Care; (1988) pp. 91-122. Apnea of prematurity is distinct from the apnea that occurs in infants at an older age.

In infants who are born before 34 weeks of gestation or who have a weight of below 1750 gm, apnea of prematurity warrants continuous monitoring. Apneic spells increase with a decrease in gestational age. Estimates are that apnea occurs in 25% of infants born at less than 37 weeks' gestation, 50% of infants born at less than 30-31 weeks, and the majority of infants born at less than 28 weeks. Spells of apnea of prematurity generally begin on the first or second day of life.

Although some treatments have been proposed, using drugs and ventilatory methods, they are not without harmful side effects. Additionally, the costs are substantial due to the prolonged monitoring and treatment.

Examples of some therapeutic modes in use include: sensory stimulation; homeostatic equilibration; supplementation with approximately 25-30% oxygen; continuous positive airway pressure and mechanical ventilation; and drug therapy. Drug therapy includes the use of methylxanthines. A principle concern of the use of methylxanthines is that they may induce alterations in lipid synthesis of brain cells that could have a bearing on the infant's future development. Volpe, *Effects of Methylxanthines on Lipid Synthesis in Developing Neural*

*System*, Semin. Perinatal 5:395 (1981). Doxapram has also been suggested for possible use to treat apnea in neonates.

There remains a need for an appropriate therapy for treating apnea of prematurity.

SUMMARY OF THE INVENTION

The present invention provides a method for improving ventilation during sleep. To this end, the present invention provides a method of using branched-chain amino acids as an effective therapy for sleep apnea.

The branched-chain amino acid composition can be administered either parenterally or enterally, and can be administered alone or in combination with other nutrients. The branched-chain amino acid composition of the present invention functions as a ventilatory stimulator during sleep and does not result in any adverse effects either to the patient or to the sleep patterns of the patient.

In an embodiment of the present invention, a method for treating apnea of prematurity is provided. The method comprising administering to an infant an effective amount of a composition including branched chain amino acids.

In an embodiment, the composition includes at least approximately 50% branched chain amino acids.

In an embodiment, the infants receive at least 50% BCAA mixed with Travasol ® or Trophamine, dextrose, and lipid. Significant reduction in work of breathing, improvement in dynamic compliance, and duration of apneic episodes, particularly those greater than 15 seconds, has been observed using the composition of the present invention.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
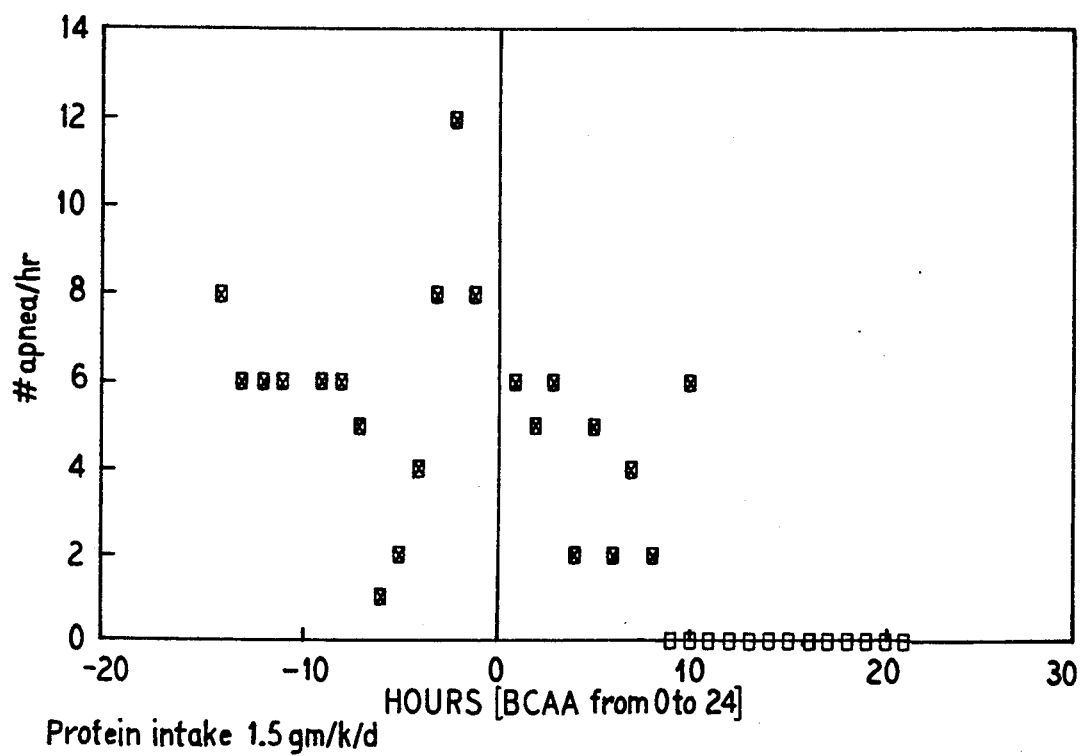
FIG. 1 illustrates graphically the number of apneic spells for a patient versus administration time of the composition of the present invention.

Branched-chain amino acid infusions have been shown to increase ventilatory drive when compared to conventional amino acid solutions and 5% dextrose. The infusion of amino acids increases ventilation by shifting the response curve of minute ventilation to arterial carbon dioxide tension to the left during carbon dioxide inhalation.

The inventor of the present invention has found that by altering an amino acid composition, by increasing the amount of branched-chain amino acids, an increase in ventilation and a decrease in arterial carbon dioxide tension is achieved. Branched-chain amino acids induce a larger decrease in arterial carbon dioxide tension and a larger increase in ventilatory response to carbon dioxide than a conventional amino acid solution. It has been found that branched-chain amino acids will induce a larger decrease in arterial carbon dioxide tension and a larger increase in ventilatory response to carbon dioxide than a conventional amino acid solution when infused for four hours after an overnight fast. This affect is even more dramatic when the infusion is continued over a 48 hour period.

In an embodiment, the composition of the present invention that includes branched-chain amino acids can be used to treat apnea of prematurity.

By way of example, and not limitation, examples of the present invention will now be set forth.

EXAMPLES

Example No. 1

Five non-smoking healthy male volunteers (24 to 32 years of age), with no sleep disorders and who were not taking any medication, were studied. The subjects were studied on three separate nights. One night was a control that did not include the infusion of any solution and on the other two nights a continuous infusion of either BCAA (3.5% solution of 100% BCAA) or placebo (½ normal saline) was administered. The composition of the BCAA solution used was as follows:

| Composition of BCAA Solution (per 100 ml) | |
|---|---|
| Isoleucine | 1.38 g |
| Leucine | 1.38 g |
| Valine | 1.24 g |
| Total nitrogen | 443 mg |

The BCAAs/saline solutions were infused in a single blind crossover design with infusion/control nights randomly assigned within every patient. The patients were allowed no food intake after 5 pm and no stimulants (i.e., coffee) were allowed after 12 noon on the study days.

The subjects were admitted at 8:30 p.m. to a sleep-awake center. On the nights they were to receive an infusion, a peripheral cannula was inserted into the patients for the infusion. Sleep stages were studied using a 12-channel polysomnographic monitor (Grass P78). Chest wall movements were measured with a pneumograph consisting of a small circular rubber bellows attached around the chest. The bellows were connected to a volumetric pressure transducer. The signals were amplified with a DC amplifier. Air flow at the mouth and nose was measured by a thermistor placed at each nostril and the upper lip in the midline position. An ear oximeter (Ohmeda Biox 3700) was used to record oxyhemoglobin saturation. End tidal $CO_2$ was measured using a capnograph (Normocap, Datex, Finland), the sampling tube was placed in the nasopharynx. A continuous electrocardiogram ran during the night.

The infusion solutions were started one hour prior to the estimated bedtime. The infusion rate was 100 ml/hour and infusion was discontinued in the morning at 7:30 a.m. The BCAA dose was 4 grams of amino acids/hour responding 0.443 grams of nitrogen/hour.

The end-tidal $CO_2$ levels during nights of BCAA infusion (44±5 mmHg) were lower than during control nights (C: 52±1 mmHg, $p<0.01$ and S: 50±3 mmHg, $p<0.05$). There was a trend ($p<0.2$) of increase in $O_2$-saturation levels. The results are set forth in Table 1 below:

TABLE 1

The highest end-tidal $CO_2$ ($ETCO_2$), and lowest $SaO_2$ values during the study nights; C (control nights without infusion), BCAA and NaCl

|  | C | BCAA | NaCl |
|---|---|---|---|
| $ETCO_2$ (mmHg) | 52 ± 1.4 | 44 ± 5.3 | 50 ± 2.6 |

TABLE 1-continued

The highest end-tidal CO$_2$ (ETCO$_2$), and lowest SaO$_2$ values during the study nights; C (control nights without infusion), BCAA and NaCl

|  | C | BCAA | NaCl |
|---|---|---|---|
| SaO$_2$ (%) | 93 ± 1.6 | 95 ± 2.3 | 94 ± 0.5 | there was no significant change in the amount of REM sleep. The amount of stage 3 sleep and the combined stage 3 and 4 sleep were greater during BCAA nights than control nights (7.2±4.0% vs 4.3±2.8%, p<0.05 and 15.9±3.0% vs. 12.3±3.9%, p<0.02, respectively). Sleep efficiency was slightly, but not significantly, decreased with either infusion (BCAA: 87±8, NaCl: 87±8, and C: 92±10). One patient had 10 apneic episodes on the control night, 5 with NaCl, but none with BCAA infusion. The polysomnographic data is summarized in Table 2 below:

TABLE 2

The polysomnograph data from the three study nights

|  | C | BCAA | NaCl |
|---|---|---|---|
| Sleep efficiency | 92 ± 10 | 87 ± 8 | 87 ± 8 |
| Sleep latency | 2.1 ± 3.2 | 4.7 ± 4.9 | 2.1 ± 1.5 |
| Stage 1 sleep | 3.2 ± 2.3 | 5.3 ± 5 | 4.5 ± 1.8 |
| Stage 2 sleep | 59 ± 3.7 | 59 ± 3.2 | 62 ± 5.5 |
| Stage 3 sleep | 4.3 ± 2.8 | 7.2 ± 4 | 9 ± 6 |
| Stage 4 sleep | 8 ± 6 | 7 ± 3 | 6 ± 5 |
| Stage 3 & 4 | 12 ± 4 | 16 ± 3 | 15 ± 9 |
| REM sleep | 25 ± 6 | 20 ± 5 | 19 ± 4 |
| REM latency | 80 ± 36 | 95 ± 109 | 73 ± 17 |
| Apneas | 2.5 ± 5 | 0 ± 0 | 1.3 ± 2.5 |
| Hypopneas | 7 ± 11 | 4 ± 6 | 4 ± 6 |

All subjects had slightly hypercapnic highest end-tidal CO$_2$ values during both control nights and BCAA infusion decreased it to eucapnic levels (range 44–36 mmHg). BCAA infusions did not cause hypocapnia and thus the risks of causing hyperventilation and respiratory alkalosis appears negligible. There was not a significant change in oxygen SaO$_2$ during BCAA infusion, which was to be expected as all patients were in good health and had normal saturation levels (range for lowest value was 93–99%). One subject had apneas during control nights but not during BCAA infusion. Although some investigators have indicated that the hypoxic ventilatory drive is more important in sleep apnea patients than hypercapnic ventilatory drive, the results indicate enhancing the respiratory drive by BCAA infusion assists in normalizing the breathing patterns during sleep in healthy subjects.

The sleep patterns, even with the infusion of BCAAs, remained largely intact. There was no significant change in the amount of REM sleep or REM latency. The amount of stage 3 sleep and combined stage 3 and 4 sleep increased significantly during BCAA nights when compared to control night without infusion. The study demonstrates that BCAA infusions indeed affect neurophysiological functions during sleep. The accentuation of the respiratory effects of amino acids by BCAA can have important clinical relevance for patients with decreased ventilatory drive due to anesthesia, medication, prolonged administration of 5% dextrose, or sleep apneas due to different origins.

Example No. 2

A 31 year old, morbidly obese white female was admitted with a diagnosis of increasing shortness of breath, peripheral cyanosis secondary to morbid obesity with a history of sleep disturbance (diagnosis: sleep apnea versus obesity hypoventilation). The patient had been previously maintained on home oxygen therapy and nasal CPAP. The patient presented increasing dyspnea on exertion of a half a block, four to five pillow orthopnea, frequent night awakenings, and chronic peripheral edema. The patient also had perioral and peripheral cyanosis, complained of feeling very tired in the mornings, and had a history of lightheadedness and diffuse constant chronic numbness in the morning.

During admission, the patient's blood gases were measured. The blood gases were arterial PO2 67 mmHg, arterial PC02 50 mmHg and PH 7.34. Vital capacity was 1.1 liter (predicted 3.8), forced expiratory volume 0.81 liter (predicted 2.7).

A past medical history was taken and was significant in that a gastric stapling performed at St. Luke's eight years prior, had became "unbuttoned."

The medicines the patient was given, at the time of admission included Lasix and Aminophylline. The patient was also started on a 600 calorie diet. The patient's blood gases were: arterial PO2 46, arterial PCO2 51, PH 7.42 while awake.

The patient began a regimen of branched chain amino acid parenteral nutrition. The patient was started on a Branchamin ® infusion of 4%, available from Clintec Nutrition, Deerfield, Ill., at 100 ml/hr in the hospital. This was well tolerated. After the patient left the hospital, home infusions were instituted on a nightly basis at a rate of 100 ml/hr of 4% Branchamin ®, available from Clintec Nutrition. Soon thereafter, symptomatic improvement occurred.

Following nine months of these infusions, the patient remained stable at home, was more energetic upon awakening, and many of her morning symptoms had resolved completely. The patient's vital capacity had increased to 1.17 l and her FEV1 had increased to 0.181 l/sec. Feelings of lightheadedness and other symptoms previously reported had improved as did the perioral and peripheral cyanosis the patient had experienced upon awakening.

The increase in vital capacity and FEVI demonstrates that the Branchamin ® has improved the patient's sleep apnea.

Example 3

Two premature infants in whom apneic and/or bradycardic spells were recorded over more than 24 hours, and who receive parenteral nutrition, were enrolled in a study, after informed parental consent. The results of the study are set forth in FIGS. 1 and 2. Infant #1, FIG. 1, was born at 32 weeks, was 30 days of age at the time of the study and had a body weight of 1655 grams. Infant #2, FIG. 2, was born at 31 weeks, was 11 days of age at the time of the study and had a body weight of 1340 grams.

Each infant was studied on three consecutive days. The results of the analysis are set forth graphically in FIGS. 1 and 2.

Day 1

During approximately 24 hours, the infants received a parenteral nutrition schedule with regular amino acid solution (containing 30% of BCAA), according to gestational and postnatal age, weight, and caloric requirement. For Infant #1, protein intake was 1.5 gm/kg/d, for Infant #2, protein intake was 2.5 gm/kg/d. The number and character of the apneic and/or bradycardic spells was recorded.

Day 2

On Day 2, each infant received an infusion of BCAA-enriched parenteral feeding solution. The BCAA-enriched solution was obtained by mixing 4% Branchamin ® (Clintec Nutrition, Deerfield, Ill.) with an amino acid solution which contains 30% of BCAA creating a composition including 53% BCAA. The solution was prepared under meticulous aseptic conditions, and under laminar flow. The rate of the BCAA-enriched infusion and the amount of nitrogen supplied was the same as on the previous day.

Apneic spells and/or bradycardic episodes and the time of their occurrence were recorded during the 24 hour of BCAA-enriched infusion.

One and a half ml venous blood was drawn for amino acid concentration, ammonia and blood gases analysis, before and after the infusion with BCAA-enriched solutions.

Day 3

Regular amino acid solution, 30% BCAA, was again infused, and apneic and/or bradycardic spells were recorded.

Figure 2:
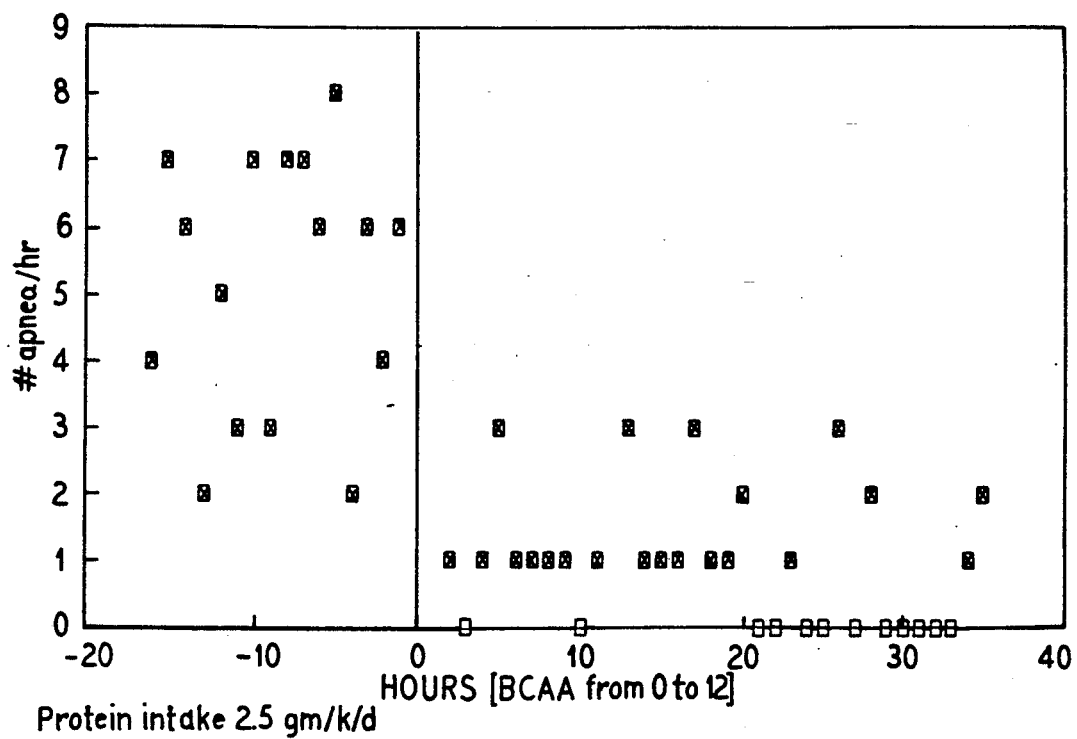
FIG. 2 illustrates graphically, for a second patient, apneic spells versus administration time of the composition of the present invention.

FIGS. 1 and 2 illustrate, graphically, the results of the study for Infants #1 and #2, respectively. Apnea spells per hour greater than or equal to 15 seconds are graphed versus hours. Day 1 of the study is illustrated at time −20 hours to 0 hours. Day 2 of the study is illustrated as beginning at 0 hours. In Infant #1, the Day 2 infusion is illustrated as proceeding from 0 to 24 hours. For Infant #2, the Day 2 infusion is illustrated as proceeding from 0 to 12 hours. Day 3 of the study is illustrated after the termination of Day 2, 24 and 12 hours, respectively.

Example 4

By way of example, and not limitation, a contemplated example of the present invention is as follows:

A premature infant gestational age 32 weeks, weighing 1340 grams with respiratory distress, was given total parenteral nutrition (TPN) as part of the standard neonatal ICU care. TPN consisted of Intralipid ®, available from Clintec Nutrition Company, Dextrose, and Trophamine available from McGaw. Trophamine was given at 1.5 g amino acids/kilogram body weight/per day. The number of apneic spells and pulmonary function, i.e., dynamic compliance and work of breathing, were monitored and are presented below.

On day 11 of the ICU stay the patient's TPN prescription was modified to contain 53% branched chain amino acids provided as a mixture of Trophamine and 4% BranchAmin ®, available from Clintec Nutrition Company. Dynamic compliance, work of breathing and number of apneic spells improved dramatically. Data gathered at 20 hours post-branched chain amino acid infusion are given below.

|  | TPN (Trophamine) | TPN Trophamine + 4% BranchAmin ® |
|---|---|---|
| Dynamic Compliance (total) (ml/cmH$_2$O) | 3.68 | 27.58 |
| Work of Breathing (gm-cm/kg) | 15.78 | 10.00 |
| # Apneic Spells (>15 sec) per hour | 6 | 1 |

Not only does the composition of the present invention reduce the incidence of apneic episodes in the premature infant, but additionally, improves dynamic compliance and work of breathing improving the premature infant's pulmonary functions.

It is believed that if the composition is administered enterally, approximately 0.003 grams to about 0.625 grams of branched chain amino acids should be administered per kg of body weight per hour. The lower end considers continuous infusion of small volumes while the upper end considers the administration of a bolus or other large dose.

If the composition is administered parenterally, approximately 0.01 grams to about 0.125 grams of branched chain amino acids per kg of body weight should be administered per hour.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method of treating apnea due to an underdeveloped respiratory drive center and pulmonary functions in a premature infant comprising the steps of:
administering to a premature infant having apnea due to an underdeveloped respiratory drive center a therapeutically effective amount of a composition comprising at lest one branched-chain amino acid.

2. The method of claim 1 wherein the composition is administered parenterally.

3. The method of claim 1 wherein the composition is administered enterally.

4. The method of claim 1 including the step of administering enterally approximately 0.003 grams to about 0.625 grams of branched-chain amino acids per kg of body weight per hour.

5. The method of claim 1 including the step of administering parenterally approximately 0.01 grams to about 0.125 grams of branched-chain amino acids per kg of body weight per hour.

6. The method of claim 1 wherein the composition includes at least approximately 50% branched chain amino acids.

7. A method of treating apnea of prematurity due to an underdeveloped respiratory drive center comprising the step of administering to an infant suffering from apnea of prematurity due to an underdeveloped respiratory drive center a solution including at least one amino acid chosen from the group consisting of valine, leucine, and isoleucine.

8. The method of claim 7 wherein the solution is administered parenterally.

9. The method of claim 7 wherein the solution is administered enterally.

10. The method of claim 7 including the step of administering enterally approximately 0.003 grams to about 0.625 grams of branched chain amino acids per kg of body weight per hour.

11. The method of claim 7 including the step of administering parenterally approximately 0.01 grams to about .125 grams of branched-chain amino acids per kg of body weight per hour.

12. The method of claim 7 wherein the composition includes approximately 50% branched chain amino acids.

13. The method of claim 7 wherein the composition includes dextrose.

14. The method of claim 7 wherein the composition includes a lipid.

15. A method of treating apnea due to an underdeveloped respiratory drive center in a neonate comprising administering to the neonate a composition comprising at least approximately 50% branched-chain amino acid.

16. The method of claim 15 including the step of administering enterally approximately 0.003 grams to about 0.625 grams of branched-chain amino acids per kg of body weight per hour.

17. The method of claim 15 including the step of administering parenterally approximately 0.01 grams to about 0.125 grams of branched-chain amino acids per kg of body weight per hour.

18. The method of claim 15 wherein the composition includes dextrose.

19. The method of claim 15 wherein the composition includes a lipid.

* * * * *